United States Patent [19]

Chatterjee et al.

[11] Patent Number: 5,912,155
[45] Date of Patent: Jun. 15, 1999

[54] **CLONED DNA POLYMERASES FROM *THERMOTOGA NEAPOLITANA***

[75] Inventors: Deb K. Chatterjee, N. Potomac; A. John Hughes, Jr., Germantown, both of Md.

[73] Assignee: Life Technologies, Inc., Rockville, Md.

[21] Appl. No.: 08/370,190

[22] Filed: Jan. 9, 1995

Related U.S. Application Data

[63] Continuation-in-part of application No. 08/316,423, Sep. 30, 1994, abandoned.

[51] Int. Cl.⁶ .............................. C12N 9/12; C12N 15/54
[52] U.S. Cl. ..................... 435/194; 536/23.2; 435/320.1; 435/252.3; 435/252.33
[58] Field of Search ................................ 435/194, 320.1, 435/252.3, 252.33; 536/23.2

[56] References Cited

U.S. PATENT DOCUMENTS

| | | | |
|---|---|---|---|
| H1531 | 5/1996 | Blumentals et al. | 435/194 |
| 4,795,699 | 1/1989 | Tarbor et al. | 435/5 |
| 4,889,818 | 12/1989 | Gelfand et al. | 435/194 |
| 5,047,342 | 9/1991 | Chatterjee | 435/194 |
| 5,614,365 | 3/1997 | Tabor et al. | 435/6 |
| 5,624,833 | 4/1997 | Gelfand et al. | 435/194 |

FOREIGN PATENT DOCUMENTS

| | | |
|---|---|---|
| 0 655 506 | 5/1995 | European Pat. Off. |
| 92 03556 | 3/1992 | WIPO . |
| 92 06200 | 4/1992 | WIPO . |
| 92 06202 | 4/1992 | WIPO . |
| 96 38568 | 12/1996 | WIPO . |
| WO 96/41014 | 12/1996 | WIPO . |

OTHER PUBLICATIONS

Derbyshire et al., The 3'–5' exonuclease of DNA polymerase I of *Escherichia coli*: contribution of each amino acid at the active site to the reaction, *EMBO J.* 10: 17–24 (1990).

Derbyshire et al., Genetic and Crystallographic Studies of the 3', 5'–Exonucleolytic Site of DNA Polymerase I, *Science*, vol. 240, 199–201 (1988).

Polesky et al., Side Chains Involved in Catalysis of the Polymerase Reaction of DNA Polymerase I from *Escherichia coli*, *J. Bio. Chem.*, vol. 267, No. 12: 8417–8428 (1992).

Polesky et al., Identification of Residues Critical for the Polymerase Activity of the Klenow Fragment of DNA Polymerase I from *Escherichia coli, J.Bio. Chem.*, vol. 265, No. 24;14579–14591 (1990).

D.L. Ollis et al., Structure of large fragment of *Escherichia coli* DNA polymerase I complexed with dTMP, *Nature*, vol. 313: 762–766 (1985).

C.M. Joyce, Can DNA polymerase I (Klenow fragment) serve as a model for other polymerases?, *Current Opin.Struct. Bio.* vol 1: 123–129 (1991).

Bernad et al., A Conserved 3'–5' Exonuclease Active Site in Prokaryotic and Eukaryotic DNA Polymerases, *Cell*, vol. 59: 219–228 (1989).

D. Gutman et al., Conserved sites in the 5'–3' exonuclease domain of *Escherichia coli* DNA polymerase, *Nuc. Acids Res.*, vol. 21, No. 18: 4406–4407 (1993).

D.K. Braithwaite et al., Compilation, alignment, and phylogenetic relationships of DNA polymerases, *Nuc. Acids Res.*, vol. 21, No. 4: 787–802 (1993).

Shengyu et al., Heat–Stable DNA Polymerase I Large Fragment Resolves Hairpin Structure In DNA Sequencing, *Scientia Sinica* (Series B), vol. XXX; 503–507 (1987).

Jannasch et al., "*Thermotoga neapolitana* sp. nov. of the Extremely Thermophilic, Eubacterial Genus Thermotoga," *Archives of Microbiology* 150(1):103–104 (1988).

Slater et al., "DNA Polymerase I of *Thermatoga neopolitane* (Tne) and Mutant Derivatives," Seventh International Genome Sequencing and Analysis Conference, Sep. 16–20, 1995, Abstract.

Bergquist et al., Genetics and Potential Biotechnological Applications of Thermophilic and Extremely Thermophilic Microorganisms, *Biotech. Genet. Eng. Rev.* 5:199–244 (1987).

Chien et al., Deoxyribonucleic Acid Polymerase from Extreme Thermophile *Thermus aquaticus, J. Bacteriology* 127:1550–1557 (1976).

Darzins and Chakrabarty, Cloning of Genes Controlling Alginate Biosynthesis from a Mucoid Cystic Fibrosis Isolate of *Pseudomonas aeruginosa, J. Bacteriol.* 159:9–18 (1984).

Elie et al., Thermostable DNA polymerase from the archaebacterium *Sulfolobus acidocaldarius Eur. J. Biochem.* 178:619–626 (1989).

Huber et al., *Thermotoga maritima* sp. nov. represents a new genus of unique extremely thermophilic eubacteria growing up to 90 degree celsius, *Arch. Microbiol.* 144:324–333 (1986).

Huser et al., Isolation and characterization of a novel extremely thermophilic, anaerobic, chemo–organothrophic eubacterium, *FEMS Microbiology Letters* 37:121–127 (1986).

Kaboev et al., Purification and Properties of Deoxyribonucleic Acid Polymerase from *Bacillus stearothermophilus, J. Bacteriol.* 145(1):21–26 (1981).

Kaledin et al., Isolation and Properties of DNA Polymerase from Extremely Thermophilic Bacterium *Thermus aquaticus* YT1, *Biokhimiya* 45:644–51 (1980).

(List continued on next page.)

*Primary Examiner*—Keith D. Hendricks
*Attorney, Agent, or Firm*—Sterne, Kessler, Goldstein & Fox P.L.L.C.

[57] ABSTRACT

The invention relates to a substantially pure thermostable DNA polymerase from *Thermotoga neapolitana* (Tne). The Tne DNA polymerase has a molecular weight of about 100 kilodaltons and is more thermostable than Taq DNA polymerase. The present invention also relates to the cloning and expression of the Tne DNA polymerase in *E. coli*, to DNA molecules containing the cloned gene, and to host cells which express said genes. The Tne DNA polymerase of the invention may be used in well-known DNA sequencing and amplification reactions.

47 Claims, 4 Drawing Sheets

OTHER PUBLICATIONS

Kelly et al., Extremely Thermophilic Archaebacteria: Biological and Engineering Consideration, *Biotechnol. Prog.* 4(2):47–62 (1988).

Klimczak et al., Purification and Characterization of DNA Polymerase from the Archaebacterium *Methanobacterium thermoautotrophicum, Biochemistry* 25:4850–4855 (1986).

Lin et al., Cloning and expressing of T4 DNA polymerase, *Proc. Natl. Acad. Sci. USA* 84:7000–7004 (1987).

Minkley et al., *Escherichia coli* DNA Polymerase I, *J. Biol. Chem.* 259(16):10386–10392 (1984).

Rossi et al., Structure and Properties of a Thermophilic and Thermostable Polymerase from *Sulfolobus solfataricus, System. Appl. Microbiol.* 7:337–341 (1986).

Sagner et al., Rapid filter assay for the detection of DNA polymerase activity: direct identification of the gene for the DNA polymerase from *Thermus aquaticus, Gene* 97:119–123 (1991).

Simpson et al., Purification and some properties of a thermostable DNA polymerase from a Thermotoga species, *Biochem. Cell Biol.* 86:1292–1296 (1990).

Stenesh et al., DNA Polymerase from Mesophilic and Thermophilic Bacteria, I. Purification and properties of DNA polymerase from *Bacillus licheniformis* and *Bacillus stearothermophilus, Biochim. Biochys. Acta* 272:156–166 (1972).

Windberger et al., *Thermotoga thermarum* sp. nov. and *Thermotoga neapolitana* occurring in African continental solfataric springs, *Arch. Microbiol.* 151: 506–512 (1989).

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 23 base pairs
        (B) TYPE: nucleic acid
        (C) STRANDEDNESS: both
        (D) TOPOLOGY: both (xi) SEQUENCE DESCRIPTION: SEQ ID NO:1:

GAGCTCACGG GGGATGCAGG AAA                                       23

(2) INFORMATION FOR SEQ ID NO:2:

(i) SEQUENCE CHARACTERISTICS:
        (A) LENGTH: 1306 base pairs
        (B) TYPE: nucleic acid
        (C) STRANDEDNESS: both
        (D) TOPOLOGY: both (xi) SEQUENCE DESCRIPTION: SEQ ID NO:2:

```
ATGGCGAGAC TATTTCTCTT TGATGGCACA GCCCTGGCCT ACAGGGCATA TTACGCCCTC      60
GACAGATCCC TTTCCACATC CACAGGAATT CCAACGAACG CCGTCTATGG CGTTGCCAGG     120
ATGCTCGTTA AATCATAAAG GAACACATTA TACCCCAAAA GGACTACGCG GCTGTGGCCT     180
TCGACAAGAA GGCAGCGACG TTCAGACACA AACTGCTCGT AAGCGACAAG GCGCAAAGGC     240
CAAAGACGCC GGCTCTTCTA GTTCAGCAGC TACCTTACAT CAAGCGGCTG ATAGAAGCTC     300
TTGGTTTCAA AGTGCTGGAG CTGGAAGGGA TACGAAGCAG ACGATATCAT CGCCACGCTT     360
GCAGCAAGGG CTGCACGTTT TTTGATGAGA TTTTCATAAT AACCGGTGAC AAGGATATGC     420
TTCAACTTGT AAACGAGAAG ATAAAGGTCT GGAGAATCGT CAAGGGGATA TCGGATCTTG     480
AGCTTTACGA TTCGAAAAAG GTGAAAGAAA GATACGGTGT GGAACCACAT CAGATACCGG     540
ATCTTCTAGC ACTGACGGGA GACGACATAG ACAACATTCC CGGTGTAACG GGAATAGGTG     600
AAAAGACCGC TGTACAGCTT CTCGGCAAGT ATAGAAATCT TGAATACATT CTGGAGCATG     660
CCCGTGAACT CCCCCAGAGA GTGAGAAAGG CTCTCTTGAG AGACAGGGAA GTTGCCATCC     720
TCAGTAAAAA ACTTGCAACT CTGGTGACGA ACGCACCTGT TGAAGTGGAC TGGGAAGAGA     780
TGAAATACAG AGGATACGAC AAGAGAAAAC TACTTCCGAT ATTGAAAGAA CTGGAGTTTG     840
CTTCCATCAT GAAGGAACTT CAACTGTACG AAGAAGCAGA ACCCACCGGA TACGAAATCG     900
TGAAGGATCA TAAGACCTTC GAAGATCTCA TCGAAAAGCT GAAGGAGGTT CCATCTTTTG     960
CCCTGGACCT TGAAACGTCC TCCTTGACCG TTCAACTGTG AGATAGTCGG CATCTCCGTG    1020
TCGTTTCAAA CCGAAAACAG CTTATTACAT TCCACTTCAT CACAGAACGC CCACAATCTT    1080
GATGAAACAC TGGTGCTGTC GAAGTTGAAA GAGATCCTCG AAGACCCGTC TTCGAAGATT    1140
GTGGGTCAGA ACCTGAAGTA CGACTACAAG GTTCTTATGG TAAAGGGTAT ATCGCCAGTT    1200
TATCCGCATT TTGACACGAT GATAGCTGCA TATTTGCTGG AGCCAAACGA GAAAAATTCA    1260
ATCTCGAAGA TCTGTCTTTG AAATTTCTCG GATACAAAAT GACGTC                   1306
```

(2) INFORMATION FOR SEQ ID NO:3:

(i) SEQUENCE CHARACTERISTICS:
        (A) LENGTH: 434 amino acids
        (B) TYPE: amino acid
        (C) STRANDEDNESS: unknown
        (D) TOPOLOGY: unknown (xi) SEQUENCE DESCRIPTION: SEQ ID NO:3:

```
Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Thr Gly Ile Pro Thr
            20                  25                  30

Asn Ala Val Tyr Gly Val Ala Arg Met Leu Val Ile Ile Lys Glu His
            35                  40                  45

Ile Ile Pro Gln Lys Asp Tyr Ala Ala Val Ala Phe Asp Lys Lys Ala
        50                  55                  60

Ala Thr Phe Arg His Lys Leu Leu Val Ser Asp Lys Ala Gln Arg Pro
65                  70                  75                  80

Lys Thr Pro Ala Leu Leu Val Gln Gln Leu Pro Tyr Ile Lys Arg Leu
                85                  90                  95

Ile Glu Ala Leu Gly Phe Lys Val Leu Glu Leu Glu Gly Tyr Glu Ala
            100                 105                 110

Asp Asp Ile Ile Ala Thr Leu Ala Ser Lys Gly Cys Thr Phe Phe Asp
```

-continued

```
                    115                 120                 125
Glu Ile Phe Ile Ile Thr Gly Asp Lys Asp Met Leu Gln Leu Val Asn
        130                 135                 140
Glu Lys Ile Lys Val Trp Arg Ile Val Lys Gly Ile Ser Asp Leu Glu
145                 150                 155                 160
Leu Tyr Asp Ser Lys Lys Val Lys Glu Arg Tyr Gly Val Glu Pro His
                165                 170                 175
Gln Ile Pro Asp Leu Leu Ala Leu Thr Gly Asp Asp Ile Asp Asn Ile
                180                 185                 190
Pro Gly Val Thr Gly Ile Gly Glu Lys Thr Ala Val Gln Leu Leu Gly
                195                 200                 205
Lys Tyr Arg Asn Leu Glu Tyr Ile Leu Glu His Ala Arg Glu Leu Pro
        210                 215                 220
Gln Arg Val Arg Lys Ala Leu Leu Arg Asp Arg Glu Val Ala Ile Leu
225                 230                 235                 240
Ser Lys Lys Leu Ala Thr Leu Val Thr Asn Ala Pro Val Glu Val Asp
                245                 250                 255
Trp Glu Glu Met Lys Tyr Arg Gly Tyr Asp Lys Arg Lys Leu Leu Pro
                260                 265                 270
Ile Leu Lys Glu Leu Glu Phe Ala Ser Ile Met Lys Glu Leu Gln Leu
        275                 280                 285
Tyr Glu Glu Ala Glu Pro Thr Gly Tyr Glu Ile Val Lys Asp His Lys
        290                 295                 300
Thr Phe Glu Asp Leu Ile Glu Lys Leu Lys Glu Val Pro Ser Phe Ala
305                 310                 315                 320
Leu Asp Leu Glu Thr Ser Ser Leu Asp Phe Asn Cys Glu Ile Val Gly
                325                 330                 335
Ile Ser Val Ser Phe Lys Pro Lys Thr Ala Tyr Tyr Ile Pro Leu His
                340                 345                 350
His Arg Asn Ala His Asn Leu Asp Glu Thr Leu Val Leu Ser Lys Leu
        355                 360                 365
Lys Glu Ile Leu Glu Asp Pro Ser Ser Lys Ile Val Gly Gln Asn Leu
        370                 375                 380
Lys Tyr Asp Tyr Lys Val Leu Met Val Lys Gly Ile Ser Pro Val Tyr
385                 390                 395                 400
Pro His Phe Asp Thr Met Ile Ala Ala Tyr Leu Leu Glu Pro Asn Glu
                405                 410                 415
Lys Lys Phe Asn Leu Glu Asp Leu Ser Leu Lys Phe Leu Gly Tyr Lys
                420                 425                 430
Met Thr
```

CLONED DNA POLYMERASES FROM *THERMOTOGA NEAPOLITANA*

CROSS-REFERENCE TO RELATED APPLICATIONS

This application is a continuation-in-part of U.S. application Ser. No. 08/316,423, filed Sep. 30, 1994, titled "Cloned DNA Polymerases from *Thermotoga neapolitana*," the contents of which are incorporated herein in their entirety by reference, and now abandoned.

BACKGROUND OF THE INVENTION

1. Field of the Invention

The present invention relates to a substantially pure thermostable DNA polymerase. Specifically, the DNA polymerase of the present invention is a *Thermotoga neapolitana* DNA polymerase having a molecular weight of about 100 kilodaltons. The present invention also relates to cloning and expression of the *Thermotoga neapolitana* DNA polymerase in *E. coli*, to DNA molecules containing the cloned gene, and to hosts which express said genes. The DNA polymerase of the present invention may be used in DNA sequencing and amplification reactions.

2. Background Information

DNA polymerases synthesize the formation of DNA molecules which are complementary to a DNA template. Upon hybridization of a primer to the single-stranded DNA template, polymerases synthesize DNA in the 5' to 3' direction, successively adding nucleotides to the 3'-hydroxyl group of the growing strand. Thus, in the presence of deoxyribonucleoside triphosphates (dNTPs) and a primer, a new DNA molecule, complementary to the single stranded DNA template, can be synthesized.

A number of DNA polymerases have been isolated from mesophilic microorganisms such as *E. coli*. A number of these mesophilic DNA polymerases have also been cloned. Lin et al. cloned and expressed T4 DNA polymerase in *E. coli* (*Proc. Natl. Acad. Sci. USA* 84:7000–7004 (1987)). Tabor et al. (U.S. Pat. No. 4,795,699) describes a cloned T7 DNA polymerase, while Minkley et al. (*J. Biol. Chem.* 259:10386–10392 (1984)) and Chatterjee (U.S. Pat. No. 5,047,342) described *E. coli* DNA polymerase I and cloning of T5 DNA polymerase, respectively.

Although DNA polymerases from thermophiles are known, relatively little investigation has been done to isolate and even clone these enzymes. Chien et al., *J. Bacteriol.* 127:155–1557 (1976) describe a purification scheme for obtaining a polymerase from *Thermus aquaticus*. The resulting protein had a molecular weight of about 63,000 daltons by gel filtration analysis and 68,000 daltons by sucrose gradient centrifugation. Kaledin et al., *Biokhymiya* 45:644–51 (1980) disclosed a purification procedure for isolating DNA polymerase from *T. aquaticus* YET1 strain. The purified enzyme was reported to be a 62,000 dalton monomeric protein. Gelfand et al. (U.S. Pat. No. 4,889,818) cloned a gene encoding a thermostable DNA polymerase from *Thermus aquaticus*. The molecular weight of this protein was found to be about 86,000 to 90,000 daltons.

Simpson et al. purified and partially characterized a thermostable DNA polymerase from a Thermotoga species (*Biochem. Cell. Biol.* 86:1292–1296 (1990)). The purified DNA polymerase isolated by Simpson et al. exhibited a molecular weight of 85,000 daltons as determined by SDS-polyacrylamide gel electrophoresis and size-exclusion chromatography. The enzyme exhibited half-lives of 3 minutes at 95° C. and 60 minutes at 50° C. in the absence of substrate and its pH optimum was in the range of pH 7.5 to 8.0. Triton X-100 appeared to enhance the thermostability of this enzyme. The strain used to obtain the thermostable DNA polymerase described by Simpson et al. was Thermotoga species strain FjSS3-B.1 (Hussar et al., *FEMS Microbiology Letters* 37:121–127 (1986)). Other DNA polymerases have been isolated from thermophilic bacteria including *Bacillus steraothermophilus* (Stenesh et al., *Biochim. iochys. Acta* 272:156–166 (1972); and Kaboev et al., *J. Bacteriol.* 145:21–26 (1981)) and several archaebacterial species (Rossi et al., *System. Appl. Microbiol.* 7:337–341 (1986); Klimczak et al., *Biochemistry* 25:4850–4855 (1986); and Elie et al., *Eur. J. Biochem.* 178:619–626 (1989)). The most extensively purified archaebacterial DNA polymerase had a reported half-life of 15 minutes at 87° C. (Elie et al. (1989), supra). Innis et al., In *PCR Protocol: A Guide To Methods and Amplification*, Academic Press, Inc., San Diego (1990) noted that there are several extreme thermophilic eubacteria and archaebacteria that are capable of growth at very high temperatures (Bergquist et al., *Biotech. Genet. Eng. Rev.* 5:199–244 (1987); and Kelly et al., *Biotechnol Prog.* 4:47–62 (1988)) and suggested that these organisms may contain very thermostable DNA polymerases.

SUMMARY OF THE INVENTION

The present invention is directed to a thermostable DNA polymerase having a molecular weight of about 100 kilodaltons. More specifically, the DNA polymerase of the invention is isolated from *Thermotoga neapolitana* (Tne). The Thermotoga species preferred for isolating the DNA polymerase of the present invention was isolated from an African continental solfataric spring (Windberger et al., *Arch. Microbiol.* 151. 506–512, (1989)).

The Tne DNA polymerase of the present invention is extremely thermostable, showing more than 50% of activity after being heated for 60 minutes at 90° C. with or without detergent. Thus, the DNA polymerase of the present invention is more thermostable than Taq DNA polymerase.

The present invention is also directed to cloning a gene encoding a *Thermotoga neapolitana* DNA polymerase enzyme. DNA molecules containing the Tne DNA polymerase gene, according to the present invention, can be transformed and expressed in a host cell to produce a Tne DNA polymerase having a molecular weight of 100 kilodaltons. Any number of hosts may be used to express the Thermotoga DNA polymerase gene of the present invention; including prokaryotic and eukaryotic cells. Preferably, prokaryotic cells are used to express the DNA polymerase of the invention. The preferred prokaryotic hosts according to the present invention is *E. coli*.

The Tne DNA polymerase of the invention may be used in well known DNA sequencing (dideoxy DNA sequencing, cycle DNA sequencing of plasmid DNAs, etc.) and DNA amplification reactions.

DESCRIPTION OF THE PREFERRED EMBODIMENTS

Definitions

Figure 1:
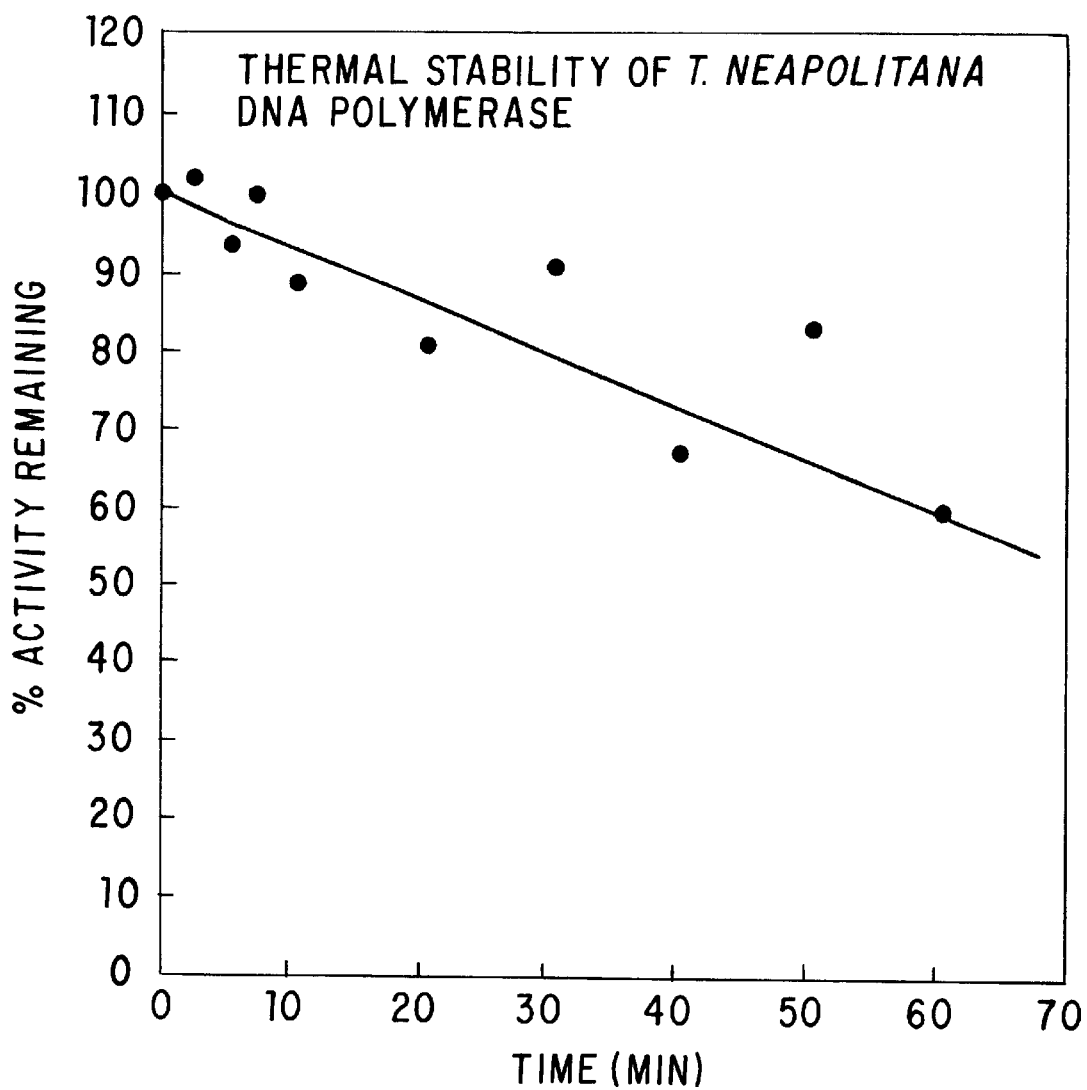
FIG. 1 demonstrates the heat stability of Tne DNA polymerase at 90° C. over time. Crude extract from *Thermotoga neapolitana* cells was used in the assay.
Figure 2:
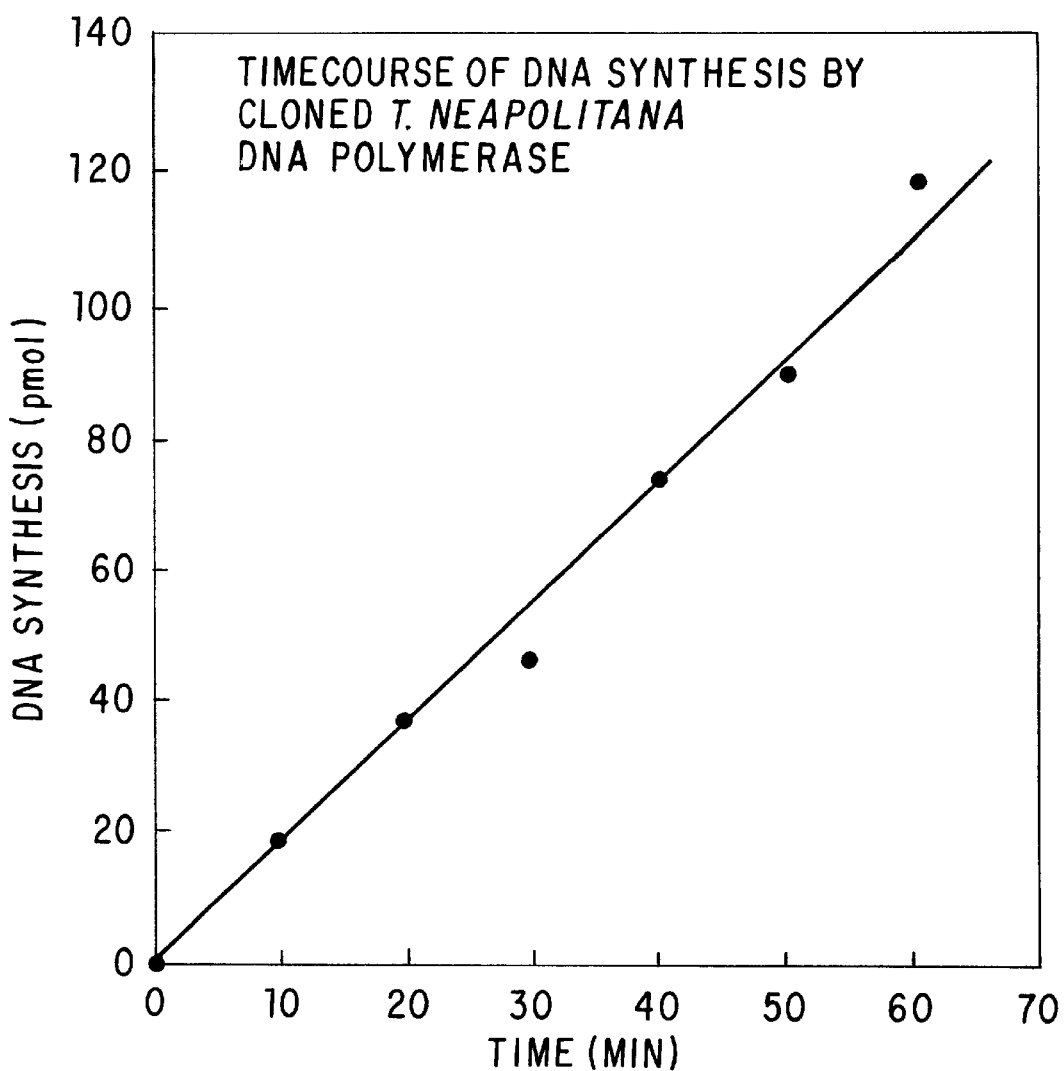
FIG. 2 shows the DNA polymerase activity in crude extracts from an *E. coli* host containing the cloned Tne DNA polymerase gene.
Figure 3:
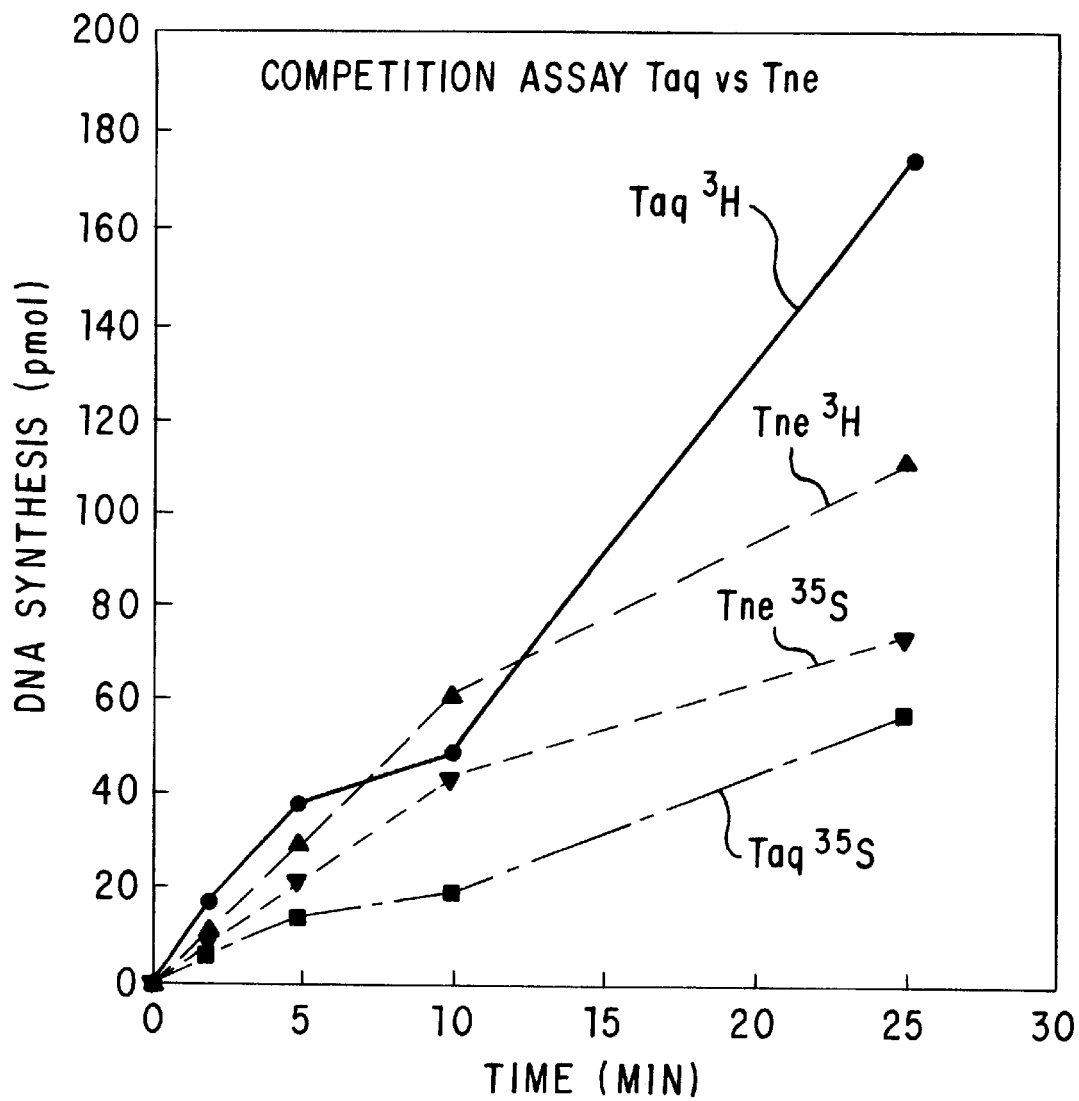
FIG. 3 compares the ability of various DNA polymerases to incorporate radioactive dATP and [αS]dATP. Tne DNA polymerase is more effective at incorporating [αS]dATP than was Taq DNA polymerase.

In the description that follows, a number of terms used in recombinant DNA technology are extensively utilized. In order to provide a clearer and consistent understanding of the specification and claims, including the scope to be given such terms, the following definitions are provided.

Cloning vector. A plasmid, cosmid or phage DNA or other DNA molecule which is able to replicate autonomously in a host cell, and which is characterized by one or a small number of endonuclease recognition sites at which such DNA sequences may be cut in a determinable fashion without loss of an essential biological function of the vector, and into which DNA may be spliced in order to bring about its replication and cloning. The cloning vector may further contain a marker suitable for use in the identification of cells transformed with the cloning vector. Markers, for example, are tetracycline resistance or ampicillin resistance.

Expression vector. A vector similar to a cloning vector but which is capable of enhancing the expression of a gene which has been cloned into it, after transformation into a host. The cloned gene is usually placed under the control of (i.e., operably linked to) certain control sequences such as promoter sequences.

Recombinant host. Any prokaryotic or eukaryotic or microorganism which contains the desired cloned genes on an expression vector, cloning vector or any DNA molecule. The term "recombinant host" is also meant to include those host cells which have been genetically engineered to contain the desired gene on the host chromosome or genome.

Host. Any prokaryotic or eukaryotic microorganism that is the recipient of a replicable expression vector, cloning vector or any DNA molecule. The DNA molecule may contain, but is not limited to, a structural gene, a promoter and/or an origin of replication.

Promoter. A DNA sequence generally described as the 5' region of a gene, located proximal to the start codon. At the promoter region, transcription of an adjacent gene(s) is initiated.

Gene. A DNA sequence that contains information necessary for expression of a polypeptide or protein. It includes the promoter and the structural gene as well as other sequences involved in expression of the protein.

Structural gene. A DNA sequence that is transcribed into messenger RNA that is then translated into a sequence of amino acids characteristic of a specific polypeptide.

Operably linked. As used herein means that the promoter controls the initiation of the expression of the polypeptide encoded by the structural gene.

Expression. Expression is the process by which a gene produces a polypeptide. It involves transcription of the gene into messenger RNA (mRNA) and the translation of such mRNA into polypeptide(s).

Substantially Pure. As used herein "substantially pure" means that the desired purified protein is essentially free from contaminating cellular contaminants which are associated with the desired protein in nature. Contaminating cellular components may include, but are not limited to, phosphatases, exonucleases, endonucleases or undesirable DNA polymerase enzymes.

Primer. As used herein "primer" refers to a single-stranded oligonucleotide that is extended by covalent bonding of nucleotide monomers during amplification or polymerization of a DNA molecule.

Template. The term "template" as used herein refers to a double-stranded or single-stranded DNA molecule which is to be amplified, synthesized or sequenced. In the case of a double-stranded DNA molecule, denaturation of its strands to form a first and a second strand is performed before these molecules may be amplified, synthesized or sequenced. A primer, complementary to a portion of a DNA template is hybridized under appropriate conditions and the DNA polymerase of the invention may then synthesize a DNA molecule complementary to said template or a portion thereof. The newly synthesized DNA molecule, according to the invention, may be equal or shorter in length than the original DNA template. Mismatch incorporation during the synthesis or extension of the newly synthesized DNA molecule may result in one or a number of mismatched base pairs. Thus, the synthesized DNA molecule need not be exactly complementary to the DNA template.

Incorporating. The term "incorporating" as used herein means becoming a part of a DNA molecule or primer.

Amplification. As used herein "amplification" refers to any in vitro method for increasing the number of copies of a nucleotide sequence with the use of a DNA polymerase. Nucleic acid amplification results in the incorporation of nucleotides into a DNA molecule or primer thereby forming a new DNA molecule complementary to a DNA template. The formed DNA molecule and its template can be used as templates to synthesize additional DNA molecules. As used herein, one amplification reaction may consist of many rounds of DNA replication. DNA amplification reactions include, for example, polymerase chain reactions (PCR). One PCR reaction may consist of 30 to 100 "cycles" of denaturation and synthesis of a DNA molecule.

Oligonucleotide. "Oligonucleotide" refers to a synthetic or natural molecule comprising a covalently linked sequence of nucleotides which are joined by a phosphodiester bond between the 3' position of the pentose of one nucleotide and the 5' position of the pentose of the adjacent nucleotide.

Nucleotide. As used herein "nucleotide" refers to a base-sugar-phosphate combination. Nucleotides are monomeric units of a nucleic acid sequence (DNA and RNA). The term nucleotide includes deoxyribonucleoside triphosphates such as dATP, dCTP, dUTP, dGTP, dTTP, or derivatives thereof. Such derivatives include, for example, dm, [αS]dATP and 7-deaza-dGTP. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels.

Thermostable. As used herein "thermostable" refers to a DNA polymerase which is resistant to inactivation by heat. DNA polymerases synthesize the formation of a DNA molecule complementary to a single-stranded DNA template by extending a primer in the 5' to 3' direction. This activity for mesophilic DNA polymerases may be inactivated by heat treatment. For example, T5 DNA polymerase activity is totally inactivated by exposing the enzyme to a temperature of 90° C. for 30 seconds. As used herein, a thermostable DNA polymerase activity is more resistant to heat inactivation than a mesophilic DNA polymerase. However, a thermostable DNA polymerase does not mean to refer to an enzyme which is totally resistant to heat inactivation and thus heat treatment may reduce the DNA polymerase activity to some extent. A thermostable DNA polymerase typically will also have a higher optimum temperature than mesophilic DNA polymerases.

Hybridization. The terms "hybridization" and "hybridizing" refers to the pairing of two complementary single-stranded nucleic acid molecules (RNA and/or DNA) to give a double-stranded molecule. As used herein, two nucleic acid molecules may be hybridized, although the base pairing is not completely complementary. Accordingly, mismatched bases do not prevent hybridization of two nucleic acid molecules provided that appropriate conditions, well known in the art, are used.

A. Cloning and Expression of *Thermotoga neapolitana* DNA Polymerase

The Thermotoga DNA polymerase of the invention can be isolated from any strain of Thermotoga which produces a DNA polymerase having the molecular weight of about 100 kilodaltons. The preferred strain to isolate the gene encoding Thermotoga DNA polymerase of the present invention is *Thermotoga neapolitana*. The most preferred *Thermotoga neapolitana* for isolating the DNA polymerase of the invention was isolated from an African continental solfataric spring (Windberger et al., *Arch. Microbiol.* 151:506–512 (1989) and may be obtained from Deutsche Sammlung von Mikroorganismen und Zellkulturen GmbH (DSM; German Collection of Microorganisms and Cell Culture) Mascheroder Weg 1b D-3300 Braunschweig, Federal Republic of Germany, as Deposit No. 5068.

To clone a gene encoding the *Thermotoga neapolitana* DNA polymerase of the invention, isolated DNA which contains the polymerase gene, obtained from *Thermotoga neapolitana* cells, is used to construct a recombinant DNA library in a vector. Any vector, well known in the art, can be used to clone the *Thermotoga neapolitana* DNA polymerase of the present invention. However, the vector used must be compatible with the host in which the recombinant DNA library will be transformed.

Prokaryotic vectors for constructing the plasmid library include plasmids such as those capable of replication in *E. coli* such as, for example, pBR322, ColE1, pSC101, pUC-vectors (pUC18, pUC19, etc.: In: *Molecular Cloning, A Laboratory Manual*, Cold Spring Harbor Laboratory Press, Cold Spring Harbor, N.Y. (1982); and Sambrook et al., In: *Molecular Cloning A Laboratory Manual* (2d ed.) Cold Spring Harbor Laboratory Press, Cold Spring Harbor, N.Y. (1989)). Bacillus plasmids include pC194, pC221, pC217, etc. Such plasmids are disclosed by Glyczan, T. In: *The Molecular Biology Bacilli*, Academic Press, York (1982), 307–329. Suitable Streptomyces plasmids include pIJ101 (Kendall et al., *J. Bacteriol* 169:4177–4183 (1987)). Pseudomonas plasmids are reviewed by John et al., (*Rad. Insec. Dis0.* 8:693–704 (1986)), and Igaki, (*Jpn. J. Bacteriol.* 33:729–742 (1978)). Broad-host range plasmids or cosmids, such as pCP13 (Darzins and Chakrabarbary, *J. Bacteriol.* 159:9–18, 1984) can also be used for the present invention. The preferred vectors for cloning the genes of the present invention are prokaryotic vectors. Preferably, pCP13 and pUC vectors are used to clone the genes of the present invention.

The preferred host for cloning the DNA polymerase gene of the invention is a prokaryotic host. The most preferred prokaryotic host is *E. coli*. However, the DNA polymerase gene of the present invention may be cloned in other prokaryotic hosts including, but not limited to, Escherichia, Bacillus, Streptomyces, Pseudomonas, Salmonella, Serratia, and Proteus. Bacterial hosts of particular interest include *E. coli* DH10B, which may be obtained from Life Technologies, Inc. (Gaithersburg, Md.).

Eukaryotic hosts for cloning and expression of the DNA polymerase of the present invention include yeast, fungi, and mammalian cells. Expression of the desired DNA polymerase in such eukaryotic cells may require the use of eukaryotic regulatory regions which include eukaryotic promoters. Cloning and expressing the DNA polymerase gene of the invention in eukaryotic cells may be accomplished by well known techniques using well known eukaryotic vector systems.

Once a DNA library has been constructed in a particular vector, an appropriate host is transformed by well known techniques. Transformed colonies are plated at a density of approximately 200–300 colonies per petri dish. Colonies are then screened for the expression of a heat stable DNA polymerase by transferring transformed *E. coli* colonies to nitrocellulose membranes. After the transferred cells are grown on nitrocellulose (approximately 12 hours), the cells are lysed by standard techniques, and the membranes are then treated at 95° C. for 5 minutes to inactivate the endogenous *E. coli* enzyme. Other temperatures may be used to inactivate the host polymerases depending on the host used and the temperature stability of the DNA polymerase to be cloned. Stable DNA polymerase activity is then detected by assaying for the presence of DNA polymerase activity using well known techniques. The gene encoding a DNA polymerase of the present invention can be cloned using the procedure described by Sagner et al., *Gene* 97:119–123 (1991), which reference is herein incorporated by reference in its entirety.

The recombinant host containing the gene encoding DNA polymerase, *E. coli* DH10B (pUC-Tne), was deposited on Sep. 30, 1994, with the Patent Culture Collection, Northern Regional Research Center, USDA, 1815 North University Street, Peoria, Ill. 61604 U.S.A. as Deposit No. NRRL B-21338.

If the Tne DNA polymerase has 3'–5' exo activity, this activity may be reduced or eliminated by mutating the Tne DNA polymerase gene. Such mutations include point mutations, frame shift mutations, deletions and insertions. Preferably, the region of the gene encoding the 3'–5' exo activity is deleted using techniques well known in the art (Sambrook et al., (1989) in: *Molecular Cloning, A Laboratory Manual* (2nd Ed.), Cold Spring Harbor Laboratory Press, Cold Spring Harbor, N.Y.).

B. Enhancing Expression of *Thermotoga neapolitana* DNA Polymerase

To optimize expression of the Thermotoga DNA polymerase of the present invention, inducible or constitutive promoters are well known and may be used to express high levels of a polymerase structural gene in a recombinant host. Similarly, high copy number vectors, well known in the art, may be used to achieve high levels of expression. Vectors having an inducible high copy number may also be useful to enhance expression of Thermotoga DNA polymerase in a recombinant host.

To express the desired structural gene in a prokaryotic cell (such as, *E. coli, B. subtilis*, Pseudomonas, etc.), it is necessary to operably link the desired structural gene to a functional prokaryotic promoter. However, the natural *Thermotoga neapolitana* promoter may function in prokaryotic hosts allowing expression of the polymerase gene. Thus, the natural Thermotoga promoter or other promoters may be used to express the DNA polymerase gene. Such other promoters may be used to enhance expression and may either be constitutive or regulatable (i.e., inducible or derepressible) promoters. Examples of constitutive promoters include the int promoter of bacteriophage λ, and the bla promoter of the β-lactamase gene of pBR322. Examples of inducible prokaryotic promoters include the major right and left promoters of bacteriophage λ ($P_L$ and $PR_R$), trp, recA, lacZ, lacI, gal, trc, and tac promoters of *E. coli*. The *B. subtilis* promoters include α-amylase (Ulmanen et al., *J. Bacteriol* 162:176–182 (1985)) and Bacillus bacteriophage promoters (Gryczan, T., In: *The Molecular Biology of Bacilli*, Academic Press, New York (1982)). Streptomyces promoters are described by Ward et al., *Mol. Gen. Genet.* 203:468478 (1986)). Prokaryotic promoters are also reviewed by Glick, *J. Ind. Microbiol.* 1:277–282 (1987); Cenatiempto, Y., *Biochimie* 68:505–516 (1986); and Gottesman, *Ann. Rev. Genet.* 18:415–442 (1984). Expression in a prokaryotic cell also requires the presence of a ribosomal binding site upstream of the gene-encoding sequence. Such ribosomal binding sites are disclosed, for example, by Gold et al., *Ann. Rev. Microbiol.* 35:365404 (1981).

To enhance the expression of Tne DNA polymerase in a eukaryotic cell, well known eukaryotic promoters and hosts may be used. Preferably, however, enhanced expression of Tne DNA polymerase is accomplished in a prokaryotic host. The preferred prokaryotic host for overexpressing this enzyme is *E. coli*.

C. Isolation and Purification of *Thermotoga neapolitana* DNA Polymerase

The enzyme(s) of the present invention (*Thermotoga neapolitana* DNA polymerase, Tne) is preferably produced by fermentation of the recombinant host containing and expressing the cloned DNA polymerase gene. However, the Tne DNA polymerase of the present invention may be isolated from any Thermotoga strain which produces the polymerase of the present invention. Fragments of the Tne polymerase are also included in the present invention. Such fragments include proteolytic fragments and fragments having polymerase activity.

Any nutrient that can be assimilated by *Thermotoga neapolitana* or a host containing the cloned Tne DNA polymerase gene may be added to the culture medium. Optimal culture conditions should be selected case by case according to the strain used and the composition of the culture medium. Antibiotics may also be added to the growth media to insure maintenance of vector DNA containing the desired gene to be expressed. Culture conditions for *Thermotoga neapolitana* have, for example, been described by Huber et Antibiotics may also be added to the growth media to insure maintenance of vector DNA containing the desired gene to be expressed. Culture conditions for *Thermotoga neapolitana* have, for example, been described by Huber et al., *Arch. Microbiol.* 144:324–333 (1986). Media formulations are also described in DSM or ATCC Catalogs and Sambrook et al., In: *Molecular Cloning, A Laboratory Manual* (2nd ed.), Cold Spring Harbor Laboratory Press, Cold Spring Harbor, N.Y. (1989).

*Thermotoga neapolitana* and recombinant host cells producing the DNA polymerase of this invention can be separated from liquid culture, for example, by centrifugation. In general, the collected microbial cells are dispersed in a suitable buffer, and then broken down by ultrasonic treatment or by other well known procedures to allow extraction of the enzymes by the buffer solution. After removal of cell debris by ultracentrifugation or centrifugation, the DNA polymerase can be purified by standard protein purification techniques such as extraction, precipitation, chromatography, affinity chromatography, electrophoresis or the like. Assays to detect the presence of the DNA polymerase during purification are well known in the art and can be used during conventional biochemical purification methods to determine the presence of these enzymes.

D. Uses of *Thermotoga neapolitana* DNA polymerase

The *Thermotoga neapolitana* DNA polymerase (Tne) of the present invention may be used in well known DNA sequencing, DNA labeling, and DNA amplification reactions. As is well known, sequencing reactions (dideoxy DNA sequencing and cycle DNA sequencing of plasmid DNA) require the use of DNA polymerases. Dideoxy-mediated sequencing involves the use of a chain-termination technique which uses a specific polymer for extension by DNA polymerase, a base-specific chain terminator and the use of polyacrylamide gels to separate the newly synthesized chain-terminated DNA molecules by size so that at least a part of the nucleotide sequence of the original DNA molecule can be determined. Specifically, a DNA molecule is sequenced by using four separate DNA sequence reactions, each of which contains different base-specific terminators. For example, the first reaction will contain a G-specific terminator, the second reaction will contain a T-specific terminator, the third reaction will contain an A-specific terminator, and a fourth reaction may contain a C-specific terminator. Preferred terminator nucleotides include dideoxyribonucleoside triphosphates (ddNTPs) such as ddATP, ddTTP, ddGTP, and ddCTP. Analogs of dideoxyribonucleoside triphosphates may also be used and are well known in the art.

When sequencing a DNA molecule, ddNTPs lack a hydroxyl residue at the 3' position of the deoxyribose base and thus, although they can be incorporated by DNA polymerases into the growing DNA chain, the absence of the 3'-hydroxy residue prevents formation of a phosphodiester bond resulting in termination of extension of the DNA molecule. Thus, when a small amount of one ddNTP is included in a sequencing reaction mixture, there is competition between extension of the chain and base-specific termination resulting in a population of synthesized DNA molecules which are shorter in length than the DNA template to be sequenced. By using four different ddNTPs in four separate enzymatic reactions, populations of the synthesized DNA molecules can be separated by size so that at least a part of the nucleotide sequence of the original DNA molecule can be determined. DNA sequencing by dideoxynucleotides is well known and is described by Sambrook et al., In: *Molecular Cloning, A Laboratory Manual*, Cold Spring Harbor Laboratory Press, Cold Spring Harbor, N.Y. (1989). As will be readily recognized, the Tne DNA polymerase of the present invention may be used in such sequencing reactions.

As is well known, detectably labeled nucleotides are typically included in sequencing reactions. Any number of labeled nucleotides can be used in sequencing (or labeling) reactions, including, but not limited to, radioactive isotopes, fluorescent labels, chemiluminescent labels, bioluminescent labels, and enzyme labels. It has been discovered that the Tne DNA polymerase of the present invention may be useful for incorporating αS nucleotides ([αS]dATP, [αS]dTTP, [αS]dCTP and [αS]dGTP) during sequencing (or labeling) reactions. For example, [$\alpha^{35}$S]dATP, a commonly used detectably labeled nucleotide in sequencing reactions, is incorporated three times more efficiently with the Tne DNA polymerase of the present invention, than with Taq DNA polymerase. Thus, the enzyme of the present invention is particularly suited for sequencing or labeling DNA molecules with [$\alpha^{35}$S]dNTPs.

Polymerase chain reaction (PCR), a well known DNA amplification technique, is a process by which DNA polymerase and deoxyribonucleoside triphosphates are used to amplify a target DNA template. In such PCR reactions, two primers, one complementary to the 3' termini (or near the 3'-termini) of the first strand of the DNA molecule to be amplified, and a second primer complementary to the 3' termini (or near the 3'-termini) of the second strand of the DNA molecule to be amplified, are hybridized to their respective DNA molecules. After hybridization, DNA polymerase, in the presence of deoxyribonucleoside triphosphates, allows the synthesis of a third DNA molecule complementary to the first strand and a fourth DNA molecule complementary to the second strand of the DNA molecule to be amplified. This synthesis results in two double stranded DNA molecules. Such double stranded DNA molecules may then be used as DNA templates for synthesis of additional DNA molecules by providing a DNA polymerase, primers, and deoxyribonucleoside triphosphates. As is well known, the additional synthesis is carried out by "cycling" the original reaction (with excess primers and deoxyribonucleoside triphosphates) allowing multiple denaturing and synthesis steps. Typically, denaturing of double stranded DNA molecules to form single stranded DNA templates is accomplished by high temperatures. The Thermotoga DNA polymerase of the present invention is a heat stable DNA polymerase, and thus will survive such thermal cycling during DNA amplification reactions. Thus, the Tne DNA polymerase of the invention is ideally suited for PCR reactions, particularly where high temperatures are used to denature the DNA molecules during amplification.

E. Kits

The *Thermotoga neapolitana* (Tne) DNA polymerase of the invention is suited for the preparation of a kit. Kits comprising Tne DNA polymerase may be used for detectably labeling DNA molecules, DNA sequencing, or amplifying DNA molecules by well known techniques, depending on the content of the kit. Such kits may comprise a carrying means being compartmentalized to receive in close confinement one or more container means such as vials, test tubes and the like. Each of such container means comprises components or a mixture of components needed to perform DNA sequencing, DNA labeling, or DNA amplification.

A kit for sequencing DNA may comprise a number of container means. A first container means may, for example, comprise a substantially purified sample of Tne DNA polymerase having the molecular weight of about 100 kilodaltons. A second container means may comprise one or a number of types of nucleotides needed to synthesize a DNA molecule complementary to DNA template. A third container means may comprise one or a number different types of dideoxynucleoside triphosphates. In addition to the above container means, additional container means may be included in the kit which comprise one or a number of DNA primers.

A kit used for amplifying DNA will comprise, for example, a first container means comprising a substantially pure Tne DNA polymerase and one or a number of additional container means which comprise a single type of nucleotide or mixtures of nucleotides. Various primers may or may not be included in a kit for amplifying DNA.

When desired, the kit of the present invention may also include container means which comprise detectably labeled nucleotides which may be used during the synthesis or sequencing of a DNA molecule. One of a number of labels may be used to detect such nucleotides. Illustrative labels include, but are not limited to, radioactive isotopes, fluorescent labels, chemiluminescent labels, bioluminescent labels and enzyme labels.

Having now generally described the invention, the same will be more readily understood through reference to the following Examples which are provided by way of illustration, and are not intended to be limiting of the present invention, unless specified.

EXAMPLE 1

Bacterial Strains And Growth Conditions

*Thermotoga neapolitana* DSM No. 5068 was grown under anaerobic conditions as described in the DSM catalog (addition of resazurin, $Na_2S$, and sulfur granules while sparging the media with nitrogen) at 85° C. in an oil bath from 12 to 24 hours. The cells were harvested by filtering the broth through Whatman #1 filter paper. The supernatant was collected in an ice bath and then centrifuged in a refrigerated centrifuge at 8,000 rpms for twenty minutes. The cell paste was stored at −70° C. prior to total genomic DNA isolation.

*E. coli* strains were grown in 2×LB broth base (Lennox L broth base: GIBCO/BRL) medium. Transformed cells were incubated in SOC (2% tryptone, 0.5% yeast extract, yeast 10 mM NaCl, 2.5M KCl, 20 mM glucose, 10 mM $MgCl_2$, and 10 mM $MgSO_4$ per liter) before plating. When appropriate antibiotic supplements were 20 mg/l tetracycline and 100 mg/l ampicillin. *E. coli* strain DH10B (Lorow et al., *Focus* 12:19–20 (1990)) was used as host strain. Competent DH10B may be obtained from Life Technologies, Inc. (LTI) (Gaithersburg, Md.).

EXAMPLE 2

DNA Isolation

*Thermotoga neapolitana* chromosomal DNA was isolated from 1.1 g of cells by suspending the cells in 2.5 ml TNE (50 mM Tris-HCl, pH 8.0, 50 mM NaCl, 10 mM EDTA) and treated with 1% SDS for 10 minutes at 37° C. DNA was extracted with phenol by gently rocking the lysed cells overnight at 4° C. The next day, the lysed cells were extracted with chloroform:isoamyl alcohol. The resulting chromosomal DNA was further purified by centrifugation in a CsCl density gradient. Chromosomal DNA isolated from the density gradient was extracted three times with isopropanol and dialyzed overnight against a buffer containing 10 mM Tris-HCl (pH 8.0) and 1 mM EDTA.

EXAMPLE 3

Construction of Genomic Libraries

The chromosomal DNA isolated in Example 2 was used to construct a genomic library in the plasmid pCP13. Briefly, 10 tubes each containing 10 μkg of *Thermotoga neapolitana* chromosomal DNA was digested with 0.01 to 10 units of Sau3Al for 1 hour at 37° C. A portion of the digested DNA was tested in an agarose (1.2%) gel to determine the extent of digestion. Samples with less than 50% digestion were pooled, ethanol precipitated and dissolved in TE. 6.5 μg of partially digested chromosomal DNA was ligated into 1.5 μg of pCP13 cosmid which had been digested with BamHI restriction endonuclease and dephosphorylated with calf intestinal alkaline phosphatase. Ligation of the partially digested Thermotoga DNA and BamHI cleaved pCP13 was carried out with T4 DNA ligase at 22° C. for 16 hours. After ligation, about 1 μg of ligated DNA was packaged using λ-packaging extract (obtained from Life Technologies, Inc., Gaithersburg, Md.). DH10B cells (Life Tech. Inc.) were then infected with 100 μl of the packaged material. The infected cells were plated on tetracycline containing plates. Serial dilutions were made so that approximately 200 to 300 tetracycline resistant colonies were obtained per plate.

EXAMPLE 4

Screening for Clones Expressing *Thermotoga neapolitana* DNA Polymerase

Identification of the *Thermotoga neapolitana* DNA polymerase gene of the invention was cloned using the method of Sanger et al., *Gene* 97:119–123 (1991) which reference is herein incorporated in its entirety. Briefly, the *E. coli* tetracycline resistant colonies from Example 3 were transferred to nitrocellulose membranes and allowed to grow for 12 hours. The cells were then lysed with the fumes of chloroform:toluene (1:1) for 20 minutes and dried for 10 minutes at room temperature. The membranes were then treated at 95° C. for 5 minutes to inactivate the endogenous *E. coli* enzymes. Surviving DNA polymerase activity was detected by submerging the membranes in 15 ml of polymerase reaction mix (50 mM Tris-HCl (pH 8.8), 1 mM MgCl$_2$, 3 mM β-mercaptoethanol, 10 μM dCTP, dGTP, dTTP, and 15 μCi of 3,000 Ci/mmol [α$^{32}$P]dATP) for 30 minutes at 65° C.

Using autoradiography, three colonies were identified that expressed a *Thermotoga neapolitana* DNA polymerase. The cells were grown in liquid culture and the protein extract was made by sonication. The presence of the cloned thermostable polymerase was confirmed by treatment at 90° C. followed by measurement of DNA polymerase activity by incorporation of radioactive deoxyribonucleoside triphosphates into acid insoluble DNA. One of the clones, expressing Tne DNA polymerase, contained a plasmid designated pCP13-32 was used for further study.

EXAMPLE 5

Subcloning of Tne DNA polymerase

Figure 4:
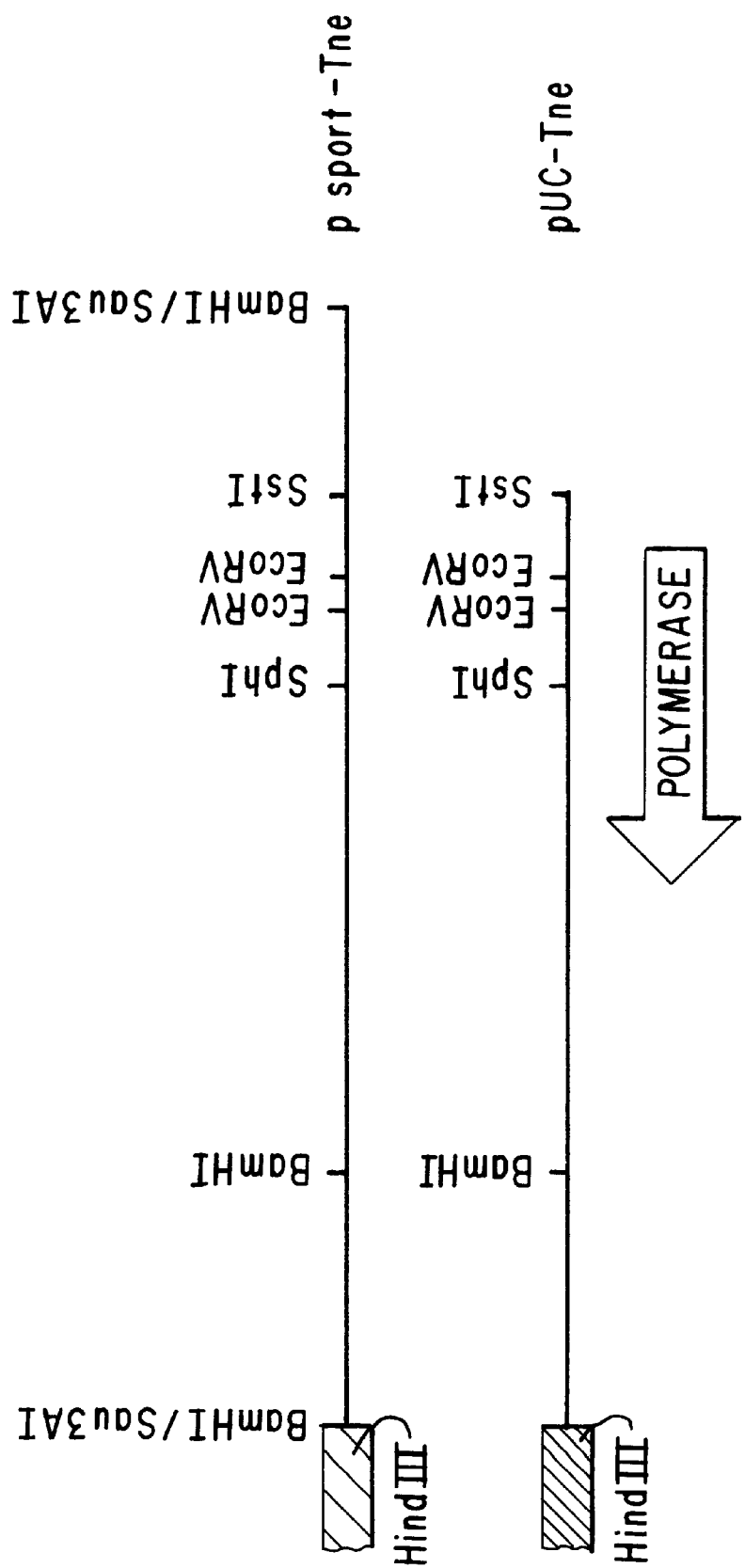
FIG. 4 shows the restriction map of the approximate DNA fragment which contains the Tne DNA polymerase gene in pSport 1 and pUC19.

Since the pCP13-32 clone expressing the Tne polymerase gene contains about 25 kb of *T. neapolitana* DNA, we attempted to subclone a smaller fragment of the Tne polymerase gene. The molecular weight of the Tne polymerase purified from *E. coli*/pCP13-32 was about 100 Kd. Therefore, a 2.5–3.0 kb DNA fragment will be sufficient to code for full-length polymerase. A second round of Sau3A partial digestion similar to Example 3 was done using pCP13-32 DNA. In this case, a 3.5 kb region was cut out from the agarose gel, purified by Gene Clean (BIO 101, LaJolla, Calif.) and ligated into plasmid pSport 1 (Life Technologies, Inc.) which had been linearized with BamHI and dephosphoylated with calf intestinal phosphatase. After ligation, DH10B was transformed and colonies were tested for DNA polymerase activity as described in Example 4. Several clones were identified that expressed Tne DNA polymerase. One of the clones (pSport-Tne) containing about 3 kb insert was further characterized. A restriction map of the DNA fragment is shown in FIG. 4. Further, a 2.7 Kb Hind III-SstI fragment was subcloned into pUC19 to generate pUC19-Tne. *E. coli*/pUC19-Tne also produced Tne DNA polymerase.

The Tne polymerase clone was sequenced by methods known in the art. The nucleotide sequence obtained of the 5' end prior to the start ATG is shown in SEQ ID NO:1. The nucleotide sequence obtained which encodes the Tne polymerase is shown in SEQ ID NO:2. When SEQ ID NO:2 is translated it does not produce the entire amino acid sequence of the Tne polymerase due to frame shift errors in the nucleotide sequence set forth in SEQ ID NO:2. However, an amino acid sequence of the Tne polymerase was obtained by translating all three reading frames of SEQ ID NO:2, comparing these sequences with known polymerase amino acid sequences, and splicing the Tne polymerase sequence together to form the amino acid sequence set forth in SEQ ID NO:3.

EXAMPLE 6

Purification of *Thermotoga neapolitana* DNA Polymerase from *E. coli*

Twelve grams of *E. coli* cells expressing cloned Tne DNA polymerase (DH10B/pSport-Tne) were lysed by sonication (four thirty-second bursts with a medium tip at the setting of nine with a Heat Systems Ultrasonics Inc., model 375 sonicator) in 20 ml of ice cold extraction buffer (50 mM Tris HCl, pH 7.4, 8% glycerol, 5 mM mercaptoethanol, 10 mM NaCl, 1 mM EDTA, 0.5 mM PMSF). The sonicated extract was heated at 80° C. for 15 min. and then cooled in ice for 5 min. 50 mM KCl and PEI (0.4%) was added to remove nucleic acids. The extract was centrifuged for clarification. Ammonium sulfate was added at 60%, the pellet was collected by centrifugation and resuspended in 10 ml of column buffer (25 mM Tris-HCl, pH 7.4, 8% glycerol, 0.5% EDTA, 5 mM 2-mercaptoethanol, 10 mM KCl). A Blue-Sepharose (Pharmacia) column, or preferably a Toso heparin (Tosohaas) column, was washed with 7 column volumes of column buffer and eluted with a 15 column volume gradient of buffer A from 10 mM to 2M KCl. Fractions containing polymerase activity were pooled. The fractions were dialyzed against 20 volumes of column buffer. The pooled fractions were applied to a Toso650Q column (Tosohaas). The column was washed to baseline OD$_{280}$ and elution effected with a linear 10 column volume gradient of 25 mM Tris, pH 7.4, 8% glycerol, 0.5 mM EDTA, 10 mM KCl, 5 mM β-mercaptoethanol to the same buffer plus 650 mM KCl. Active fractions were pooled.

EXAMPLE 7

Characterization of Purified Tne DNA Polymerase

1. Determination of the Molecular Weight of *Thermotoga neapolitana* DNA Polymerase The molecular weight of 100 kilodaltons was determined by electrophoresis in a 12.5% SDS gel by the method of Laemmli, U.K., *Nature* (Lond.) 227:680–685 (1970). Proteins were detected by staining with Coomassie brilliant blue. A 10 Kd protein ladder (Life Technologies, Inc.) was used as standard.

2. Method for Measuring Incorporation of [α$^{35}$S]-dATP Relative to $^3$H-dATP Incorporation of [αS]dATP was evaluated in a final volume of 500 μl of reaction mix, which was preincubated at 72° C. for five minutes, containing either a [$^3$H]TTP nucleotide cocktail (100 μM each TTP, dATP, dCTP, dGTP with [$^3$H]TTP at 90.3 cpm/pmol), a nucleotide cocktail containing [αS]dATP as the only source of dATP (100 μM each [αS]dATP, dCTP, dGTP, TTP with [α$^{35}$S]dATP at 235 cpm/pmol), or a mixed cocktail (50 μM [αS]dATP, 50 μM dATP, 100 μM TTP, 100 μM dCTP, 100 μM dGTP with [$^{35}$αS]dATP at 118 cpm/pmol and [$^3$H]TTP at 45.2 cpm/ pmol). The reaction was initiated by the addition of 0.3 units of *T. neapolitana* DNA polymerase or *T. aquaticus* DNA polymerase. At the times indicated a 25 μl aliquot was removed and quenched by addition of ice cold EDTA to a final concentration of 83 mM. 20 μl aliquots of the quenched reaction samples were spotted onto GF/C filters. Rates of incorporation were compared and expressed as a ratio of *T. neapolitana* to *T. aquaticus*. The incorporation of $[\alpha^{35}S]$ dATP by *T. neapolitana* DNA polymerase was three-fold higher than that of *T. aquaticus* DNA polymerase.

EXAMPLE 8

Reverse Transcriptase Activity $(A)_n:(dT)_{12-18}$ is the synthetic template primer used most frequently to assay for reverse transcriptase activity of DNA polymerases. It is not specific for retroviral-like reverse transcriptase, however, being copied by many prokaryotic and eukaryotic DNA polymerases (Modak and Marcus, *J. Biol. Chem.* 252:11–19 (1977); Gerard et al., *Biochem.* 13:1632–1641 (1974); Spadari and Weissbach, *J. Biol. Chem.* 249:5809–5815 (1974)). $(A)_n:(dT)_{12-18}$ is copied particularly well by cellular, replicative DNA polymerases in the presence of $Mn^{++}$, and much less efficiently in the presence of $Mg^{++}$ (Modak and Marcus, *J. Biol. Chem.* 252:11–19 (1977); Gerard et al., *Biochem.* 13:1632–1641 (1974); Spadari and Weissbach, *J. Biol. Chem.* 249:5809–5815 (1974)). In contrast, most cellular, replicative DNA polymerases do not copy the synthetic template primer $(C)_n:(dG)_{12-18}$ efficiently in presence of either $Mn^{++}$ or $Mg^{++}$, but retroviral reverse transcriptases do. Therefore, in testing for the reverse transcriptase activity of a DNA polymerase with synthetic template primers, the stringency of the test increases in the following manner from least to most stringent: $(A)_n:(dT)_{12-18}$ $(Mn^{++})<(A)_n:(dT)_{12-18}$ $(Mg^{++})<<(C)_n:(dG)_{12-18}$ $(Mn^{++})<(C)_n:(dG)_{12-18}$ $(Mg^{++})$.

The reverse transcriptase activity of *Thermotoga neapolitana* (Tne) DNA polymerase was compared with *Thermus thermophilus* (Tth) DNA polymerase utilizing both $(A)_n:(dT)_{20}$ and $(C)_n:(dG)_{12-18}$. Reaction mixtures (50 μl) with $(A)_n:(dT)_{20}$ contained 50 mM Tris-HCl (pH 8.4), 100 μM $(A)_n$, 100 μM $(dT)_{20}$, and either 40 mM KCl, 6 mM $MgCl_2$, 10 mM dithiothreitol, and 500 μM [$^3H$]dTTP (85 cpm/pmole), or 100 mM KCl, 1 mM $MnCl_2$, and 200 μM [$^3H$]dTTP (92 cpm/pmole). Reaction mixtures (50 μl) with $(C)_n:(dG)_{12-18}$ contained 50 mM Tris-HCl (pH 8.4), 60 μM $(C)_n$, 24 μM $(dG)_{12-18}$, and either 50 mM KCl, 10 mM $MgCl_2$, 10 mM dithiothreitol, and 100 μM [$^3H$]dGTP (132 cpm/pmole), or 100 mM KCl, 0.5 mM $MnCl_2$, and 200 μM [$^3H$]dGTP (107 cpm/pmole). Reaction mixtures also contained either 2.5 units of the Tth DNA polymerase (Perkin-Elmer) or 2.5 units of the Tne DNA polymerase. Incubations were at 45° C. for 10 min followed by 75° C. for 20 min.

The table shows the results of determining the relative levels of incorporation of Tne and Tth DNA polymerase with $(A)_n:(dT)_{20}$ and $(C)_n:(dG)_{12-18}$ in the presence of $Mg^{++}$ and $Mn^{++}$. Tne DNA polymerase appears to be a better reverse transcriptase than Tth DNA polymerase under reaction conditions more specific for reverse transcriptase, i.e., in the presence of $(A)_n:(dT)_{20}$ with $Mg^{++}$ and $(C)_n:(dG)_{12-18}$ with $Mn^{++}$ or $Mg^{++}$.

| DNA Polymerase Activity of Tth and Tne DNA Polymerase with $(A)_n:(dT)_{20}$ and $(C)_n:(dG)_{12-18}$ | | | | |
|---|---|---|---|---|
| | DNA Polymerase Activity (pMoles Complementary [$^3H$]dNTP Incorporated) | | | |
| | $(A)_n:(dT)_{20}$ | | $(C)_n:(dG)$ | |
| Enzyme | $Mg^{++}$ | $Mn^{++}$ | $Mg^{++}$ | $Mn^{++}$ |
| Tne | 161.8 | 188.7 | 0.6 | 4.2 |
| Tth | 44.8 | 541.8 | 0 | 0.9 |

What is claimed is:

1. A substantially pure thermostable *Thermotoga neapolitana* DNA polymerase, wherein said DNA polymerase is a Pol I-type polymerase.

2. The substantially pure thermostable *Thermotoga neapolitana* DNA polymerase as claimed in claim 1, wherein said polymerase has a molecular weight of about 100 kDa.

3. The substantially pure thermostable *Thermotoga neapolitana* DNA polymerase as claimed in claim 1, wherein said DNA polymerase has the amino acid sequence of the *Thermotoga neapolitana* DNA polymerase produced by *Escherichia coli* DH10B/pUC-Tne.

4. A substantially pure *Thermotoga neapolitana* DNA polymerase having a molecular weight of about 100 kDa, or fragments thereof having DNA polymerase activity.

5. The substantially pure *Thermotoga neapolitana* DNA polymerase or fragments as claimed in claim 4, wherein said DNA polymerase has the amino acid sequence of the *Thermotoga neapolitana* DNA polymerase produced by *Escherichia coli* DH10B/pUC-Tne.

6. The substantially pure *Thermotoga neapolitana* DNA polymerase or fragments thereof as claimed in claim 4, wherein said DNA polymerase comprises the amino acid sequence of SEQ ID NO:3.

7. The substantially pure *Thermotoga neapolitana* DNA polymerase or fragments thereof as claimed in claim 4, wherein said DNA polymerase has reverse transcriptase activity.

8. The substantially pure *Thermotoga neapolitana* DNA polymerase or fragments thereof as claimed in claim 4, wherein said DNA polymerase has an enhanced rate of incorporation of dATP relative to [$^{35}$S] *Thermus aguaticus* DNA polymerase.

9. A substantially pure *Thermotoga neapolitana* DNA polymerase, wherein said polymerase is encoded by a DNA molecule having the restriction map of the *Thermotoga neapolitana* DNA polymerase gene as shown in FIG. 4.

10. A fragment of a substantially pure *Thermotoga neapolitana* DNA polymerase, wherein said polymerase is encoded by a DNA molecule having the restriction map of the *Thermotoga neapolitana* DNA polymerase gene as shown in FIG. 4 and said fragment has DNA polymerase activity.

11. The fragment of a substantially pure *Thermotoga neapolitana* DNA polymerase as claimed in claim 10, wherein said fragment has reverse transcriptase activity.

12. The fragment of a substantially pure *Thermotoga neapolitana* DNA polymerase as claimed in claim 10, wherein said fragment has an enhanced rate of incorporation of [$^{35}$S] dATP relative to *Thermus aquaticus* DNA polymerase.

13. An isolated nucleic acid molecule encoding a thermostable *Thermotoga neapolitana* DNA polymerase, wherein said DNA polymerase is a Pol I-type polymerase.

14. The isolated nucleic acid molecule as claimed in claim 13, wherein said nucleic acid molecule encodes a *Thermotoga neapolitana* DNA polymerase having a molecular weight of about 100 kDa.

15. The isolated nucleic acid molecule as claimed in claim 13, wherein said DNA polymerase has the amino acid sequence of the *Thermotoga neapolitana* DNA polymerase produced by *Escherichia coli* DH10B/pUC-Tne.

16. An isolated nucleic acid molecule encoding a *Thermotoga neapolitana* DNA polymerase having a molecular weight of 100 kDa, or fragments thereof having DNA polymerase activity.

17. The isolated nucleic acid molecule as claimed in claim 16, wherein said DNA polymerase has the amino acid sequence of the *Thermotoga neapolitana* DNA polymerase produced by *Escherichia coli* DH10B/pUC-Tne.

18. The isolated nucleic acid molecule as claimed in claim 16, wherein said DNA polymerase comprises the amino acid sequence of SEQ ID NO:3.

19. The isolated nucleic acid molecule as claimed in claim 16, wherein said nucleic acid molecule comprises the nucleotide sequence of SEQ ID NO:2.

20. The isolated nucleic acid molecule as claimed in claim 16, wherein said DNA polymerase has reverse transcriptase activity.

21. The isolated nucleic acid molecule as claimed in claim 16, wherein said DNA polymerase has an enhanced rate of incorporation of [$^{35}$S] dATP relative to *Thermus aquaticus* DNA polymerase.

22. An isolated nucleic acid molecule comprising a gene coding for *Thermotoga neapolitana* DNA polymerase, wherein said gene coding for *Thermotoga neapolitana* DNA polymerase has the restriction map of the *Thermotoga neapolitana* DNA polymerase gene as shown in FIG. 4.

23. An isolated nucleic acid molecule comprising a fragment of a gene coding for *Thermotoga neapolitana* DNA polymerase, wherein said gene coding for *Thermotoga neapolitana* DNA polymerase has the restriction map of the *Thermotoga neapolitana* DNA polymerase gene as shown in FIG. 4 and said fragment encodes a polypeptide having DNA polymerase activity.

24. The isolated nucleic acid molecule as claimed in claim 23, wherein said polypeptide has reverse transcriptase activity.

25. The isolated nucleic acid molecule as claimed in claim 23, wherein said polypeptide has an enhanced rate of incorporation of [$^{35}$S]dATP relative to *Thermus aguaticus* DNA polymerase.

26. A recombinant nucleic acid molecule, wherein said recombinant nucleic acid molecule comprises the polynucleotide sequence of an isolated nucleic acid molecule as claimed in any one of claims 13, 16, 22, and 23.

27. The isolated nucleic acid molecule as claimed in any one of claims 13, 16, 22, and 23, wherein said nucleic acid molecule is a DNA molecule.

28. The isolated nucleic acid molecule as claimed in claim 27, wherein said DNA molecule further comprises a promoter.

29. The isolated nucleic acid molecule as claimed in claim 28, wherein said promoter is an inducible promoter selected from the group consisting of: a tac promoter, a trp promoter, and a trc promoter.

30. A recombinant host cell transformed with a gene encoding a thermostable *Thermotoga neapolitana* DNA polymerase, wherein said DNA polymerase is a Pol I-type polymerase.

31. A recombinant host cell transformed with a gene encoding a *Thermotoga neapolitana* DNA polymerase having a molecular weight of about 100 kDa, or fragments thereof having DNA polymerase activity.

32. The recombinant host cell as claimed in claim 31, wherein said recombinant host cell can produce a *Thermotoga neapolitana* DNA polymerase having the amino acid sequence of the *Thermotoga neapolitana* DNA polymerase produced by *Escherichia coli* DH10B/pUC-Tne.

33. The recombinant host cell as claimed in claim 31, wherein said recombinant host cell is *Escherichia coli* DH10B/pUC-Tne.

34. The recombinant host cell as claimed in claim 31, wherein said recombinant host cell comprises a gene for *Thermotoga neapolitana* DNA polymerase having the restriction map of the *Thermotoga neapolitana* DNA polymerase gene as shown in FIG. 4.

35. The recombinant host cell as claimed in claim 31, wherein said recombinant host cell comprises a fragment of the gene for *Thermotoga neapolitana* DNA polymerase, wherein said DNA polymerase gene has the restriction map of the *Thermotoga neapolitana* DNA polymerase gene as shown in FIG. 4.

36. The recombinant host cell as claimed in any one of claims 30 and 31, wherein said host cell is prokaryotic.

37. The recombinant host cell as claimed in claim 36, wherein said host cell is *Escherichia coli*.

38. The recombinant host cell as claimed in claim 37, wherein said host cell is *Escherichia coli* DH10B/pUC-Tne as deposited with the Agricultural Research Service Patent Culture Collection, Northern Regional Research Center, USDA, under Deposit No. NRRL B-21338.

39. A method of producing a thermostable *Thermotoga neapolitana* DNA polymerase, said method comprising:
    (a) culturing a cell transformed with a gene encoding said thermostable *Thermotoga neapolitana* DNA polymerase or fragments thereof having DNA polymerase activity;
    (b) expressing said gene; and
    (c) isolating said DNA polymerase or fragment thereof having DNA polymerase activity from said cell or the cell culture of said cell.

40. The method of producing a thermostable *Thermotoga neapolitana* DNA polymerase as claimed in claim 39, wherein said cell is a recombinant host cell.

41. The method of producing a thermostable DNA polymerase as claimed in claim 39, wherein said thermostable DNA polymerase has a molecular weight of about 100 kDa.

42. The method of producing a thermostable DNA polymerase as claimed 39, wherein said thermostable DNA polymerase has the amino acid sequence of the *Thermotoga neapolitana* DNA polymerase produced by *Escherichia coli* DH10B/pUC-Tne.

43. The method of producing a thermostable DNA polymerase as claimed 40, wherein said recombinant host cell is *Escherichia coli* DH10B/pUC-Tne.

44. The method of producing a thermostable DNA polymerase as claimed in claim 39, wherein said gene has the restriction map of the *Thermotoga neapolitana* DNA polymerase as shown in FIG. 4.

45. The method of producing a thermostable DNA polymerase as claimed in claim 39, wherein said host cell is a eukaryotic host cell.

46. The method of producing a thermostable DNA polymerase as claimed in claim 39, wherein said host cell is a prokaryotic host cell.

47. The method of producing a thermostable DNA polymerase as claimed 46, wherein said prokaryotic host cell is *Escherichia coli.*

* * * * *

UNITED STATES PATENT AND TRADEMARK OFFICE
CERTIFICATE OF CORRECTION

PATENT NO. : 5,912,155

DATED : June 15, 1999

INVENTORS : CHATTERJEE *et al.*

It is certified that errors appear in the above-identified patent and that said Letters Patent is hereby corrected as shown below.

In column 19, Claim 8, line 3, please delete "dATP relative to [$^{32}$S] *Thermus aguaticus*" and insert therein --[$^{32}$S]dATP relative to *Thermus aquaticus*--.

In column 20, Claim 25, line 3, please delete "*Thermus aguaticus*" and insert therein --*Thermus aquaticus*--.

Signed and Sealed this

Eighteenth Day of April, 2000

Attest:

Q. TODD DICKINSON

*Attesting Officer*    *Director of Patents and Trademarks*